(12) United States Patent
Ando

(10) Patent No.: US 9,063,112 B2
(45) Date of Patent: Jun. 23, 2015

(54) STEAM STERILIZATION INDICATOR PACK

(71) Applicant: NiGK CORPORATION, Kawagoe-shi, Saitama (JP)

(72) Inventor: Nobuyuki Ando, Kawagoe (JP)

(73) Assignee: NiGK CORPORATION, Kawagoe-shi, Saitama (JP)

(*) Notice: Subject to any disclaimer, the term of this patent is extended or adjusted under 35 U.S.C. 154(b) by 0 days.

(21) Appl. No.: 14/353,575

(22) PCT Filed: Oct. 25, 2012

(86) PCT No.: PCT/JP2012/077556
§ 371 (c)(1),
(2) Date: Apr. 23, 2014

(87) PCT Pub. No.: WO2013/065562
PCT Pub. Date: May 10, 2013

(65) Prior Publication Data
US 2014/0294696 A1 Oct. 2, 2014

(30) Foreign Application Priority Data
Oct. 31, 2011 (JP) .................. 2011-238875

(51) Int. Cl.
*G01N 21/75* (2006.01)
*G01N 31/22* (2006.01)
(Continued)

(52) U.S. Cl.
CPC .............. *G01N 31/226* (2013.01); *A61L 31/06* (2013.01); *A61L 31/14* (2013.01); *A61L 27/58* (2013.01); *A61L 2/07* (2013.01); *A61L 2/28* (2013.01)

(58) Field of Classification Search
CPC ......... A61L 31/06; A61L 31/14; A61L 27/58; A61L 2/07; A61L 2/28; G01N 31/226
USPC ......... 422/400, 401, 420, 421, 422, 423, 424, 422/425, 426, 427, 428, 429, 68.1, 82.05, 422/82.06; 436/164, 169, 170
See application file for complete search history.

(56) References Cited

U.S. PATENT DOCUMENTS 4,486,387 A 12/1984 Augurt
4,902,478 A 2/1990 Hambleton

FOREIGN PATENT DOCUMENTS

JP 01-166759 A 6/1989
JP 04-336069 A 11/1992
(Continued)

OTHER PUBLICATIONS

International Search Report of PCT/JP2012/077556, mailed Jan. 8, 2013.

*Primary Examiner* — Dennis M White
(74) *Attorney, Agent, or Firm* — Collard & Roe, P.C.

(57) ABSTRACT

Provided is a simplified steam sterilization indicator pack that is able to improve reliability of Bowie & Dick Test, and also is able to be downsized and improves handling.
A steam sterilization indicator pack comprises:
a pack which accommodates a sterilization confirmation indicator part that comprises steam transmitting adjustment layers 20, 20, of which total thickness is 5-25 mm, arranged so as to sandwich a sterilization confirmation indicator sheet 22 applying a printed pattern which colors or discolors due to contacting with steam, in a paper container 12 that passes steam more than the steam transmitting adjustment layers,
and the steam transmitting adjustment paper sheets 18 include a sheet that has at least a density of 0.75 g/cm³ so that in a case where pressurized steam is introduced at 134° C. for 3.5 minutes in a vacuumed autoclave into which the pack is put and residual air remains in the autoclave, portions of the patterns of the sterilization confirmation indicator sheet 22 that finish discoloring and other portions thereof that do not discolor can be differentiated with the naked eye.

4 Claims, 4 Drawing Sheets

(51) Int. Cl.
  *A61L 31/06* (2006.01)
  *A61L 31/14* (2006.01)
  *A61L 27/58* (2006.01)
  *A61L 2/07* (2006.01)
  *A61L 2/28* (2006.01)

(56) References Cited

FOREIGN PATENT DOCUMENTS

| | | |
|---|---|---|
| JP | H07-4409 B2 | 1/1995 |
| WO | 87/04931 | 8/1987 |

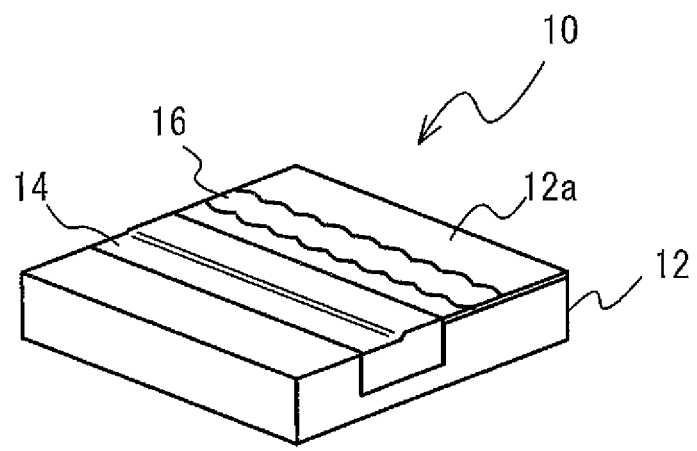
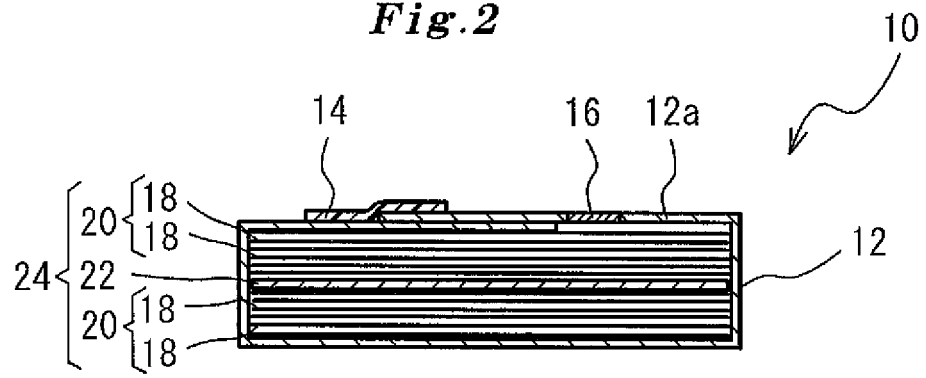

Fig.3
(a)
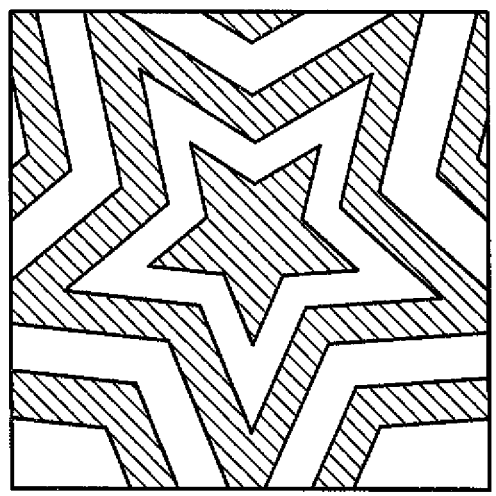
(b)
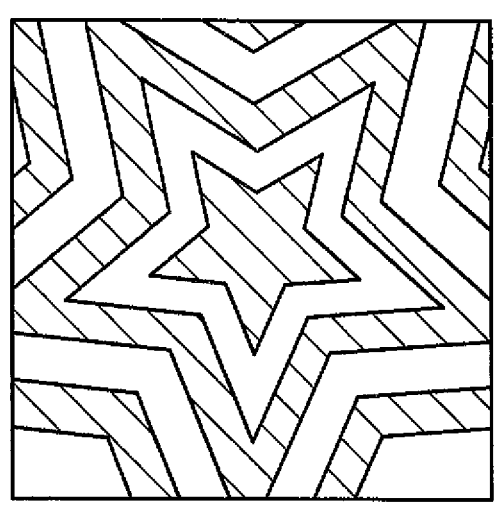

STEAM STERILIZATION INDICATOR PACK

CROSS REFERENCE TO RELATED APPLICATIONS

This application is the National Stage of PCT/JP2012/077556 filed on Oct. 25, 2012, which claims priority under 35 U.S.C. §119 of Japanese Application No. 2011-238875 filed on Oct. 31, 2011, the disclosures of which are incorporated by reference. The international application under PCT article 21(2) was not published in English.

TECHNICAL FIELD

The present invention relates to a steam sterilization indicator pack used for a test for checking whether a vacuum sterilizer by pressurized steam for sterilizing, for example medical materials, operates normally or not.

BACKGROUND OF THE INVENTION

In a field of medical treatment, one of the methods for sterilizing medical materials such as a surgical suit, a medical smock, medical appliances etc. includes a pressurized steam sterilization method in an autoclave. According to such sterilization method, the residual air in the autoclave causes a decrease in the effects on sterilization because of a potent adiabatic effect by the air. Especially, when the air is remained in the materials to be sterilized such as a surgical suit and a medical smock, even if heating by pressurized steam is performed, conduction of heat and humidity is disturbed leading a decrease in the effects on sterilization and sometimes poor sterilization. Therefore, in the pressurized steam sterilization method, the air in the materials to be sterilized that are placed in the autoclave is amply evacuated, and then the pressurized steam is provided in the autoclave to sterilize the materials.

After the air is evacuated from the autoclave by this means, to determine whether the autoclave operates normally for sufficient sterilization by the supplied pressurized steam therein, it is determined that the residual air that encumbers a flow of the pressurized steam supplied after the evacuation does not exist. One of such determination methods is Bowie and Dick Test which is termed as Bowie & Dick Test hereinafter. This Test contains following procedures. Packs sandwiching an indicator sheet that colors or discolors due to contacting with steam are inserted into the autoclave. By observing a coloring or discoloring state of the indicator sheet when pressurized steam sterilization is carried out by the prescribed procedures, it is determined that the residual air which encumbers a flow of the pressurized steam does not exist in the autoclave in order to determine whether the autoclave operates normally. In particular, this Test contains following specific procedures. Piled surgical towels are bundled to be in a certain size, the indicator sheet is disposed at the center thereof and then they are packed. After they are put into the autoclave, the autoclave is vacuumed and then the pressurized steam is introduced thereto. After heating is carried out at 134° C. for 3.5 minutes, the coloring or discoloring state of the indicator sheet is observed. If the indicator sheet is uniformly colored, it is determined that the residual air which encumbers the flow of the pressurized steam does not exist in the autoclave and thus the autoclave operates normally. On the other hand, if the indicator sheet is non-uniformly colored or discolored, it is determined that the residual air which encumbers the flow of the pressurized steam exists in the autoclave and thus the autoclave does not operate. Here, if the materials to be sterilized are put together therein, the materials are heat-sterilized again.

The appropriately plied and then bundled surgical towels as test equipment for Bowie & Dick Test having the indicator sheet at the center thereof are packed, and it is difficult to treat the packed towels due to bulkiness. Therefore, as simplified test equipment, for example, the Patent Document 1 discloses that a test pack having an indicator sheet disposed between porous bodies of piled plural non-woven fabrics entirely is covered by a paper cover sheet.

PRIOR ART DOCUMENT

[Patent Document 1] JP Examined Patent Application Publication No. 1995-4409B

SUMMARY OF THE INVENTION

Problems to be Solved by the Invention

In comparison with the prior test equipment using the piled surgical towels, the above-mentioned test pack as a simplified test equipment is downsized, more compact, and easy to handle. However, Bowie & Dick Test using such test pack can easily have dispersion of the test results because the non-woven fabrics that form the porous body of the test pack are made of individual sheets of spun-bonded polypropylene of 50-100 g/m$^2$ without a binder and therefore the non-woven fabrics are thin and have low density. Since the porous body is formed by piling 60-300 pieces of the individual sheets, it is difficult to handle the test pack due to the bulkiness. Furthermore, when such porous body is made by a lot of piled non-woven fabrics, an amount of the pressurized steam which can pass through thus porous body is decreased. Therefore, even if the heat is maintained at 134° C. for 3.5 minutes by introducing the pressurized steam into the autoclave, this indicator sheet may not color or discolor over the entire surface thereof.

The present invention was made in view of solving the above described problems, and its object is to provide a steam sterilization indicator pack used as a simplified test equipment for Bowie & Dick Test that is downsized and improved in handling, which decreases dispersion of test results by Bowie & Dick Test using the simplified test equipment as much as possible and can improve the reliability of the test.

Means for Solving the Problems

A steam sterilization indicator pack of the present invention developed to achieve the objects described above comprises:

a pack which accommodates a sterilization confirmation indicator part that comprises two steam transmitting adjustment layers arranged to sandwich a sterilization confirmation indicator sheet having a printed pattern which colors or discolors due to contacting with steam, in a paper container that passes steam more than the steam transmitting adjustment layers, and each of the steam transmitting adjustment layers is formed by stacking a plurality of steam transmitting adjustment paper sheets so that the total thickness of the two steam transmitting adjustment layers is 5-25 mm, and the steam transmitting adjustment paper sheets include a sheet that has at least a density of 0.75 g/cm$^3$ so that in a case where pressurized steam is introduced and maintained at temperature of 134° C. for heat for 3.5 minutes in a vacuumed autoclave into which the pack is put and residual air remains in the autoclave, portions of the patterns of the sterilization confirmation indicator sheet that finish coloring or discoloring by contacting with the pressurized steam which passes each of the steam transmitting adjustment layers and other portions thereof that do not finish coloring or discoloring by not contacting with the pressurized steam can be differentiated with the naked eye.

In the steam sterilization indicator pack, the steam transmitting adjustment paper sheets, which form each of the steam transmitting adjustment layers, are homogeneous and have equal thickness.

In the steam sterilization indicator pack, at least steam transmitting adjustment paper sheet in the steam transmitting adjustment paper sheets, which contacts with the sterilization confirmation indicator sheet, is a low density steam transmitting adjustment paper sheet having density of 0.6 g/cm$^3$ at the maximum, and other steam transmitting adjustment paper sheets therein include a high density steam transmitting adjustment paper sheet having density of 0.85 g/cm$^3$ at the minimum.

In the steam sterilization indicator pack, color difference: ΔE*ab between portions of the patterns of the sterilization confirmation indicator sheet that finish coloring or discoloring by contacting with the pressurized steam which passes each of the steam transmitting adjustment layers and the other portions thereof that do not finish coloring or discoloring by not contacting with the pressurized steam, is at least 10.

Effects of the Invention

The steam sterilization indicator pack of the present invention is the simplified test equipment made of paper as a whole, and thus the pack can be downsized and handling thereof can be improved favorably. The patterns which may color or discolor due to contacting with the steam are printed on the sterilization confirmation indicator sheet of the sterilization confirmation indicator part. The sterilization confirmation indicator sheet is sandwiched between the two steam transmitting adjustment layers formed to have specified thickness by stacking the steam transmitting adjustment paper sheets having specified density, and thus the dispersion of test results by Bowie & Dick Test which is caused by non-uniformity of each steam transmitting adjustment paper sheets can be decreased as much as possible. Furthermore, when Bowie & Dick Test is performed and the residual air exists in an atmosphere in which the steam sterilization indicator pack is put, among the patterns of the sterilization confirmation indicator sheet, a portion which is colored or discolored by contacting the pressurized steam and other portion which is not colored or discolored by not contacting the pressurized steam can be certainly discriminated with the naked eye. As a result, reliability of test results by Bowie & Dick Test can be improved.

BRIEF DESCRIPTION OF DRAWINGS

FIG. 1 is a perspective view showing an embodiment of a steam sterilization indicator pack of the present invention.

FIG. 2 is a cross-section view showing the steam sterilization indicator pack 10 of FIG. 1.

FIG. 3 is an elevation view showing a sterilization confirmation indicator sheet 22 of FIG. 2.

MODE FOR CARRYING OUT THE INVENTION

Figure 4:
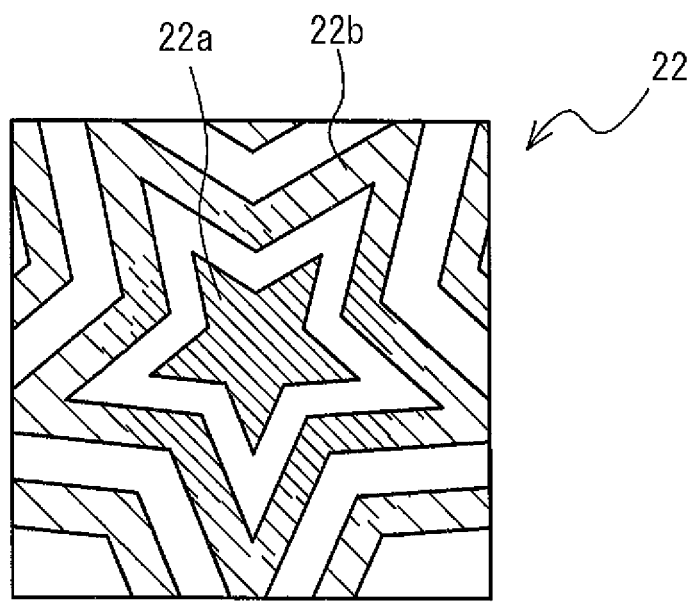
FIG. 4 is an elevation view explaining a state in which the sterilization confirmation indicator sheet 22 is partially colored or discolored.

Hereunder, embodiments to practice the present invention in detail will be explained, but the scope of the present invention is not restricted by these embodiments.

FIG. 1 shows an embodiment of a steam sterilization indicator pack of the present invention. FIG. 1 is a perspective view showing the steam sterilization indicator pack 10. As shown in FIG. 2, a sterilization confirmation indicator part 24 is accommodated in a paper container 12 as a container. In the sterilization confirmation indicator part 24, a sterilization confirmation indicator sheet 22 is sandwiched between two steam transmitting adjustment layers 20, 20. As shown in FIG. 3(a), starry patterns are drawn on the entire surface of the sterilization confirmation indicator sheet 22. In a case where the entire surface of the sterilization confirmation indicator sheet 22 contacts with steam, the entire starry patterns color or discolor as shown in FIG. 3. (b).

As shown in FIG. 4, in other case where a partial portion of the starry patterns of the sterilization confirmation indicator sheet 22 contacts with steam while the other partial portion of the starry patterns does not contact with the steam, a portion 22a without contact with the steam does not color or discolor while the other portion 22b with contact with the steam finishes coloring or discoloring. FIG. 4 indicates that in the sterilization confirmation indicator sheet 22, the portion 22a which does not color or discolor is on the central region of the starry patterns or neighborhood thereof, and the portion 22b which finishes coloring or discoloring is on the circumference region of the starry patterns. In order to discriminate the portions 22a and 22b with the naked eye certainly, it is preferable that color difference (ΔE*ab) between the portions 22a and 22b is 10 or more.

The patterns of the sterilization confirmation indicator sheet 22 may be formed by printing a thermal-metachromasy ink which colors or discolors due to contacting the steam on a paper sheet. Examples of the thermal-metachromasy ink that colors includes a composition comprising at least one selected from the group consisting of a transition metal compound such as basic carbonate, hydroxide, oxide and stearic acid compound etc. of nickel, cobalt, copper or lead; sulfur and/or sulfur compound such as zinc sulfide, thiourea, methylthiourea, 1-phenyl-2-thiourea, 1,3-diphenyl-2-thiourea, 2,2'-ditolylthiourea, and o-tolylthiourea; monoazo dye such as C.I. (Color Index) Disperse Red 58, C.I. Disperse Red 88, C.I. Disperse Red 110, C.I. Disperse Red 117, C.I. Disperse Red 137, C.I. Disperse Violet 43, and C.I. Disperse Blue 102 etc.; organic acids such as citric acid, malonic acid, phthalic acid, adipic acid, and maleic acid etc.; organic acid metal salts such as calcium salicylate, zinc salicylate, and zinc benzoate etc. Examples of the thermal-metachromasy ink, which discolors, includes a composition comprising at least one selected from the group consisting of monoazo dye such as C.I. (Color Index) Disperse Red 88, Disperse Red 117, Disperse Red 137, Disperse Violet 43 etc.; organic acids such as adipic acid etc.; organic acid metal salts such as calcium salicylate, zinc salicylate, and zinc benzoate etc.

The "pattern" in the present specification intends to include letters or figures. The pattern may be printed on only one side or on both sides of the sterilization confirmation indicator sheet 22. As shown in FIG. 3, the pattern may be printed not over entire surface of the sterilization confirmation indicator sheet 22, and it may be partially printed on a central region and a circumference region of the sterilization confirmation indicator sheet 22.

As shown in FIG. 2, plural pieces of steam transmitting adjustment paper sheets 18 are stacked in such a way that each of the steam transmitting adjustment layers 20, 20, respectively arranged to the both surface of the sterilization confirmation indicator sheet 22 in a close contact has total thickness of 5-25 mm (preferably 10-20 mm). If the total thickness of each of the steam transmitting adjustment layers 20, 20 is less than 5 mm, an amount of transmission of the steam tends to be excessive. On the other hand, if the total thickness of each of the steam transmitting adjustment layers 20, 20 is more than 25 mm, an amount of transmission of the steam tends to be too little. Each thickness of the steam transmitting adjustment layers 20, 20 is preferably equal, but it may be different from each other by about 5-10 mm at maximum. The steam transmitting adjustment paper sheets 18 for forming each steam transmitting adjustment layers 20, 20 preferably have equal thickness and homogeneity, and the thickness thereof is preferably 0.05-0.6 mm Number of the steam transmitting adjustment paper sheets 18 for forming each steam transmitting adjustment layers 20, 20 is preferably equal to each other, but may be different from each other by 10 pieces at maximum, especially about 5-10 pieces.

The steam transmitting adjustment paper sheet 18 has density of at minimum of 0.75 $g/cm^3$ (preferably 0.75-0.85 $g/cm^3$, more preferably 0.80-0.85 $g/cm^3$). If both of the steam transmitting adjustment layers 20, 20 are formed only from the steam transmitting adjustment paper sheets 18 having density of less than 0.75 $g/cm^3$, an amount of transmission of steam through the steam transmitting adjustment layer 20 tends to be excessive. In this case, when the residual air which encumbers a supplied flow of the pressurized steam in the autoclave in Bowie & Dick Test exists, the result of the test could lead to indicate "good" as the condition of the autoclave because almost entire patterns of the sterilization confirmation indicator sheet 22 color or discolor, or non-uniformly colored or discolored portions among the patterns of the sterilization confirmation indicator sheet 22 may not be discriminated with the naked eye.

If both of the steam transmitting adjustment layers 20, 20 are formed only from the steam transmitting adjustment paper sheets having density of more than 0.85 $g/cm^3$, an amount of transmission of steam through the steam transmitting adjustment layer 20 tends to decrease. In this case, when the residual air in the autoclave in Bowie & Dick Test does not exist, it is easy to discriminate with the naked eye that a portion 22*a* in the patterns of the sterilization confirmation indicator sheet 22 with contact with the steam finishes coloring or discoloring and other portion 22*b* therein without contact with the steam does not color or discolor because an amount of transmission of steam therethrough is unequal. In this situation, when the residual air does not exist in the autoclave and Bowie & Dick Test is performed by using the following steam sterilization indicator pack, entire patterns of the sterilization confirmation indicator sheet 22 color or discolor. Namely, singular or plural pieces of low-density steam transmitting adjustment paper sheets having density of 0.6 $g/cm^3$ at maximum are used for the steam transmitting adjustment paper sheets 18 which is in touch with the sterilization confirmation indicator sheet 22, and high-density steam transmitting adjustment paper sheets having density of at least 0.85 $g/cm^3$ are included in other steam transmitting adjustment paper sheets 18. Here, as the high-density steam transmitting adjustment paper sheets tends to be thin, the low-density steam transmitting adjustment paper sheets which is thicker than the high-density steam transmitting adjustment paper sheets are used so that the total thickness of each of the steam transmitting adjustment layers 20, 20 can be handily adjusted to 5-25 mm by using fewer pieces of the high-density steam transmitting adjustment paper sheets. Incidentally the low-density steam transmitting adjustment paper sheets may be used as not only the steam transmitting adjustment paper sheets 18 which is in touch with the sterilization confirmation indicator sheet 22 but also ones of neighborhood of thus steam transmitting adjustment paper sheets 18.

As shown in FIG. 2, the paper container 12 which accommodates the sterilization confirmation indicator part 24 is formed from paper whose density is lower than the steam transmitting adjustment paper sheets 18 so that the amount of transmission of the steam thereof is larger than that of the steam transmitting adjustment layers 20.

A preferable embodiment of the steam sterilization indicator pack 10 is shown more concretely. The steam sterilization indicator pack 10 is put in the autoclave, and the pressurized steam is introduced into vacuumed autoclave. When 0.2 vol % of the residual air exist in the autoclave, the steam sterilization indicator pack 10 is adjusted so that the color difference: $\Delta E^*ab$ between the peripheral portions among the patterns of the sterilization confirmation indicator sheet 22 that finish coloring or discoloring and color or discolor at the most by contacting with the pressurized steam which passes each of the steam transmitting adjustment layers 20, 20 and the central portions among the patterns that do not color or discolor by not contacting with the pressurized steam is at least 10 according to Japanese Industrial Standards Z 8722 measurement. Each of the steam transmitting adjustment layers 20, 20 stacked with plural pieces of the steam transmitting adjustment paper sheets 18 respectively has total thickness of 5-25 mm and density of 0.75-0.85 $g/cm^3$. The steam sterilization indicator pack 10 may be formed by using the steam transmitting adjustment paper sheets 18 having equal density and equal thickness. Alternatively the steam sterilization indicator pack 10 may be formed by using the steam transmitting adjustment paper sheets 18 including sheets of different density and thickness. More specifically the steam transmitting adjustment paper sheets 18 are formed by stacking the high-density steam transmitting adjustment paper sheets onto the low-density steam transmitting adjustment paper sheets. The low-density steam transmitting adjustment paper sheets is in touch with the sterilization confirmation indicator sheet 22 and has density of 0.6 $g/cm^3$ at maximum. And the high-density steam transmitting adjustment paper sheets is thinner than the low-density steam transmitting adjustment paper sheets and has density of at least 0.85 $g/cm^3$.

Figure 5:
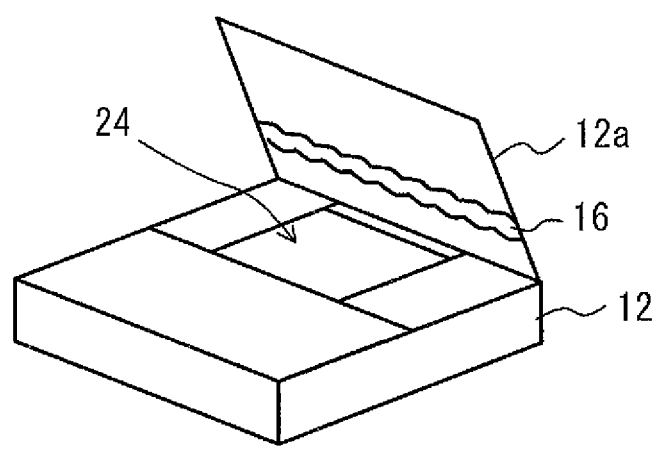
FIG. 5 is a perspective view explaining a paper container 12 formed by folding paper for shaping the paper container.
Figure 6:
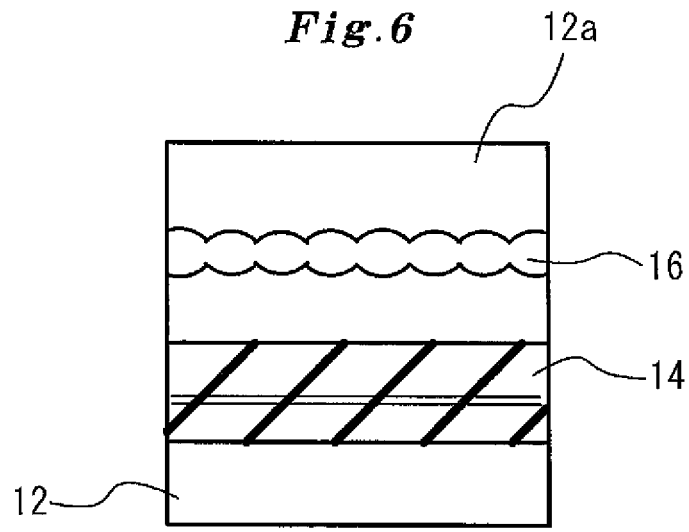
FIG. 6 is an elevation view showing another embodiment of a steam sterilization indicator pack 10 of FIG. 1.

As shown in FIG. 5, after paper for shaping a paper container is folded in a box shape to form a paper container 12 of FIG. 1, the sterilization confirmation indicator part 24 is accommodated thereinto, and then an opening of the paper container 12 is closed by a lid part 12*a*. Then edges of the lid part 12*a* are sealed by a sealing tape 14 as shown in FIG. 1. The lid part 12*a* has perforation of a cleaving part 16, so as to pick up the accommodated sterilization confirmation indicator sheet 22 while the edges of the lid part 12*a* for indicating a used stage is sealed by the sealing tape 14. The sealing tape 14 may be formed by applying a heat-sensitive ink onto a seal tape material. When the sealing tape 14 applied with the heat-sensitive ink contacts to the steam, it colors as shown in FIG. 5 and indicates the used-stage of the steam sterilization indicator pack 10.

Bowie & Dick Test is executed by using the steam sterilization indicator pack 10 shown in FIGS. 1 and 2. In this instance, the steam sterilization indicator pack 10 is put on a site where a sterilization condition is worst in the autoclave, for example a neighborhood site of an exhaust port. After the autoclave is sealed up, inside of the autoclave is maintained as a vacuum condition by using a vacuum pump (not shown). The steam is introduced into the autoclave so that pressure of the inside is turned back to normal pressure, and then the inside of the autoclave is maintained afresh as the vacuum condition by starting the vacuum pump again. Thus procedures of vacuum/turn back to the normal pressure are repeated three times so that the air in the autoclave is adequately exhausted thereby. After a pressurized steam of temperature of 134° C. is introduced into the autoclave exhausted adequately, the inside of the autoclave is maintained at a desired pressure (0.3 MPa) for 3.5 minutes of the keeping time. Then, the pressure in the autoclave is evolved, and the steam sterilization indicator pack 10 is brought out. The cleaving part 16 of the lid 12 of the steam sterilization indicator pack 10 is slit up. The sterilization confirmation indicator sheet 22 is pulled out, and then coloring or discoloring of the patterns is observed.

During the keeping time, the steam introduced into the autoclave transmits through the paper container 12 with adjusting the amount of transmission thereof by steam transmitting adjustment layers 20, 20. The steam reaches the sterilization confirmation indicator sheet 22, and makes the patterns thereof color or discolor. When the entire patterns of the sterilization confirmation indicator sheet 22 discolor as shown in FIG. 3(*b*), it is indicated that the adequate steam is reached to the entire sterilization confirmation indicator sheet 22 within 3.5 minutes of the keeping time, the residual air which encumbers the flow of the pressurized steam does not exist in the autoclave, and the autoclave operates normally for sufficient sterilization therein.

If the adequate vacuum condition (about 21.3-2.3 kPa) is not achieved in the autoclave, it causes the residual air to exists therein. When the sterilization confirmation indicator sheet 22 is pulled out from the autoclave after the inside thereof is maintained at a desired pressure (0.2-0.36 MPa, preferably 0.3 MPa) for 3.5 minutes of keeping time and the pressure in the autoclave is evolved, the starry patterns of the sterilization confirmation indicator sheet 22 partially finishes coloring or discoloring as shown in FIG. 4. The portion 22*b* which finishes coloring or discoloring and the other portion 22*a* which does not color or discolor can be certainly discriminated with the naked eye, as shown in FIG. 4. The color difference (ΔE*ab) therebetween is 10 or more. As seen above, the steam sterilization indicator pack 10 as shown in FIGS. 1 and 2 can certainly detect that the residual air which encumbers the flow of the pressurized steam exists in the autoclave and the inside of the autoclave is not maintained as the condition unsuitable for sterilization.

In the steam sterilization indicator pack 10 used for Bowie & Dick Test, the amount of the pressurized steam, which reaches to the surface of the sterilization confirmation indicator sheet 22 within the keeping time, is able to be adjusted. And when the residual air exists in the autoclave excessively, it is certainly discriminated that the sterilization confirmation indicator sheet 22 colors or discolors partially. This is important in terms of reliability of the results of Bowie & Dick Test. Herein, the steam transmitting adjustment layers 20, 20 in the steam sterilization indicator pack 10 as shown in FIGS. 1-6 are respectively formed by stacking the steam transmitting adjustment paper sheets 18 so as to be the desired thickness. Thereby, the amount of transmission of the pressurized steam which passes through the steam transmitting adjustment layers 20, 20 can be certainly adjusted. Furthermore, when residual air exists in the autoclave excessively and therefore the sterilization confirmation indicator sheet 22 colors or discolors partially, it is certainly determined with the naked eye that the residual air, which encumbers the sterilization by the pressurized steam in the autoclave and causes insufficient sterilization, exists because the color difference between the portion which finishes coloring or discoloring and the other portion which does not color or discolor is 10 or more. In consequence, the reliability of the results of Bowie & Dick Test will be improved. And since the entire steam sterilization indicator pack 10 as shown in FIGS. 1-6 is made of paper, it is simple and downsized and easy to handle.

EMBODIMENTS

Embodiments of the present invention are detailed more, but the present invention is not limited by these examples.

Example 1

A sterilization confirmation indicator sheet 22 was prepared according to the following procedures.

| | |
|---|---|
| C.I. Disperse Red 137 | 50 parts by weight |
| Phthalocyanine Blue | 5 parts by weight |
| phthalic acid | 800 parts by weight |
| butyl cellosolve solution of 20% ethyl cellulose | 1600 parts by weight |
| butyl cellosolve | 800 parts by weight |

Those ingredients were kneaded by a ball mill for 3 days to obtain an ink for screen printing. After the ink was printed onto high-quality paper, a polyethylene terephthalate (PET) film was stacked thereon to obtain a sterilization confirmation indicator sheet 22.

As steam transmitting adjustment paper sheets 18, paper having various thickness and density as shown in Table 1 was used. Plural pieces of paper shown in Table 1 were stacked onto both side of the sterilization confirmation indicator sheet 22 to form steam transmitting adjustment layers 20, 20, and a sterilization confirmation indicator part 24 was formed thereby. Thickness of each of the steam transmitting adjustment layers 20, 20 was adjusted to about 6.5 mm, and total thickness of both layers 20, 20 was adjusted to about 13 mm. And then, a paper container 12 was formed by using paper (320 g/m$^2$) which was available from NIPPON DAISHOWA PAPERBOARD Co., Ltd. The sterilization confirmation indicator part 24 was accommodated into the obtained paper container 12, an opening thereof was closed by a lid part 12*a*, and then edges of the lid part 12*a* were sealed by a sealing tape 14. A steam sterilization indicator pack 10 was prepared thereby. Incidentally, air resistance of the paper was determined according to Japanese Industrial Standard P 8117.

TABLE 1

| No. | Density | Thickness | Air Resistance |
|---|---|---|---|
| 1 | 0.680 | 0.452 | 18 |
| 2 | 0.710 | 0.403 | 12 |
| 3 | 0.680 | 0.435 | 110 |
| 4 | 0.690 | 0.080 | 63 |
| 5 | 0.700 | 0.303 | 13 |

TABLE 1-continued

| No. | Density | Thickness | Air Resistance |
|---|---|---|---|
| 6 | 0.710 | 0.203 | 17 |
| 7 | 0.810 | 0.279 | 290 |
| 8 | 0.830 | 0.425 | 160 |
| 9 | 0.810 | 0.310 | 180 |
| 10 | 0.850 | 0.288 | 230 |
| 11 | 0.850 | 0.297 | 200 |
| 12 | 0.850 | 0.288 | 230 |
| 13 | 0.890 | 0.296 | 120 |
| 14 | 0.900 | 0.240 | 130 |
| 15 | 0.930 | 0.375 | 460 |

Bowie & Dick Test was executed by using the obtained steam sterilization indicator packs 10. After each of the obtained steam sterilization indicator packs 10A was respectively put on a neighborhood site of an exhaust port in an autoclave, the autoclave was closed hermetically. And then inside of the autoclave was maintained as a vacuum condition of 16.3 kPa by using a vacuum pump. After steam was introduced into the autoclave and pressure of the inside turned back to normal pressure, the inside of the autoclave was maintained afresh as the vacuum condition by starting the vacuum pump again. Thus procedures of vacuum/turn back to the normal pressure were repeated three times so that the air in the autoclave was adequately exhausted thereby. After a pressurized steam of temperature of 134° C. was introduced into the autoclave exhausted adequately, the inside of the autoclave was maintained at a desired pressure (0.3 MPa) for 3.5 minutes. The lid part 12a of the steam sterilization indicator pack 10 was slit up, and the sterilization confirmation indicator sheet 22 was pulled out from the paper container 12. Patterns of the sterilization confirmation indicator sheet 22 discolored entirely.

Example 2 and Comparative Example 1

For comparison, the tests were executed under a condition where no residual air existed and another condition where residual air existed by intention.

Figure 7:
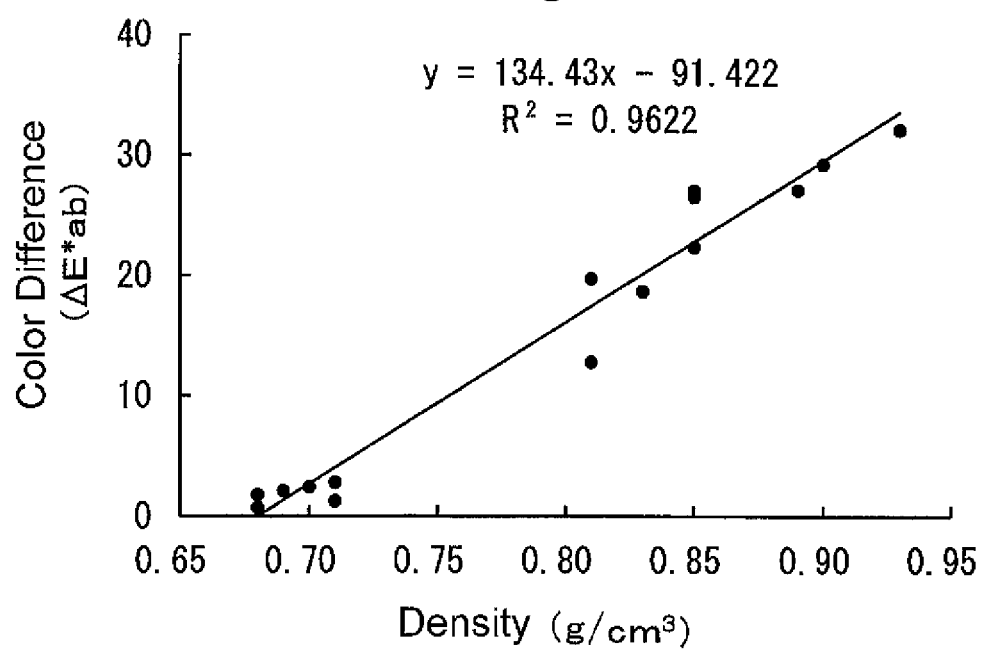
FIG. 7 is a graph showing relationship between density of the steam transmitting adjustment paper sheets 18 and color difference (ΔE*ab) of a central region of a portion 22a which was colored or discolored and a portion 22b which was not colored or discolored.

Those examples were executed as similar as Example 1, except for introducing steam of temperature of 134° C. in the autoclave where residual air was adequately exhausted and introducing air by intend, which was 380 ml converted into atmosphere pressure and 0.2 vol % to a capacity (0.196 m³) of the autoclave. The inside of the autoclave was maintained at a desired pressure (0.3 MPa) for 3.5 minutes. The cleaving part 16 of the lid part 12a of the steam sterilization indicator pack 10 was slit up, and the sterilization confirmation indicator sheet 22, whose patterns discolored partially, was pulled out from the paper container 12. Color difference: ΔE*ab between peripheral portions of the pattern of the pulled sterilization confirmation indicator sheet 22 that finished discoloring and central portions thereof that did not discolor was determined according to a 45-0 method defined in Japanese Industrial Standards Z 8722 measurement by using a color difference meter CR-321 available from KONICA MINOLTA, INC. The results are shown in FIG. 7. The density of the steam transmitting adjustment paper sheets 18 has a strong positive correlation with the color difference: ΔE*ab because the coefficient of correlation: $R^2$ was 0.9622. When the steam transmitting adjustment paper sheets 18 had density of 0.75 g/cm³ or more, which satisfies appropriate level of the present invention, the color difference: ΔE*ab between the peripheral portions of the pattern of the sterilization confirmation indicator sheet 22 that finished discoloring and central portions thereof that did not discolor was 10 or more, and therefore they were able to be discriminated with the naked eye. On the other hand, when the steam transmitting adjustment paper sheets 18 had density of less than 0.75 g/cm³, which does not satisfy appropriate level thereof, the peripheral portions of the pattern of the sterilization confirmation indicator sheet 22 that finished discoloring and central portions of the sheet 22 that did not discolor were hard to be discriminated. When air was not introduced into the autoclave by intention, the patterns of the sterilization confirmation indicator sheet 22 were discolored entirely.

Example 3 and Comparative Example 2

For comparison, the tests were executed under a condition where no residual air existed and another condition where residual air existed by intention.

Those examples were executed as similar as Example 1, except for using other steam transmitting adjustment layer 20 which was formed by allocating a piece of low-density steam transmitting adjustment paper sheet having density of 0.5 g/cm³ and thickness of 1 mm onto each side of the sterilization confirmation indicator sheet 22 respectively, and further allocating 11 pieces of high-density steam transmitting adjustment paper sheet having density of 0.92 g/cm³ and thickness of 0.49 mm onto each side thereof respectively. Therefore total thickness of each of the steam transmitting adjustment layers 20, 20 was adjusted to 13 mm. And thereby, steam sterilization indicator packs 10 were prepared as similar as Example 1.

When Bowie & Dick Test was executed by using the obtained steam sterilization indicator packs 10 as similar as Example 1, the patterns of the sterilization confirmation indicator sheet 22 ware colored entirely.

When steam of temperature of 134° C. was introduced in the autoclave from which residual air was adequately exhausted while air was introduced therein by intention, it was confirmed with the naked eye that the patterns of the sterilization confirmation indicator sheet 22 certainly discolored partially. However, when air was not introduced by intention, the patterns of the sterilization confirmation indicator sheet 22 discolored entirely.

INDUSTRIAL APPLICABILITY

The steam sterilization indicator pack of the present invention is simplified, and therefore the steam sterilization indicator pack can be downsized and handling thereof can be improved. The reliability of test results by Bowie & Dick Test using the simplified steam sterilization indicator pack can be improved, and therefore the steam sterilization indicator pack contributes to the improvement of the quality of the sterilization of the materials to be sterilized.

EXPLANATIONS OF LETTERS OR NUMERALS

10: steam sterilization indicator pack, 12: paper container, 12a: lid part, 14: sealing tape, 16: cleaving part, 18: steam transmitting adjustment paper sheets, 20: steam transmitting adjustment layer, 22: sterilization confirmation indicator sheet, 22a: portion which does not color or discolor, 22b: portion which finishes coloring or discoloring, 24: sterilization confirmation indicator part

What is claimed is:
1. A steam sterilization indicator pack comprising:
a pack which accommodates a sterilization confirmation indicator part that comprises two steam transmitting adjustment layers arranged to sandwich a sterilization confirmation indicator sheet having a printed pattern which colors or discolors due to contacting with steam, in a paper container that passes steam more than the steam transmitting adjustment layers, wherein in a case where pressurized steam is introduced in a vacuumed autoclave into which the pack is put and residual air remains in the autoclave and is maintained at 0.2 vol.% to a capacity of the autoclave, a color difference ΔE*ab between peripheral portions of the patterns of the sterilization confirmation indicator sheet that finish coloring or discoloring by contacting with the pressurized steam which passes each of the steam transmitting adjustment layers and central portions thereof that do not finish coloring or discoloring by not contacting with the pressurized steam, is at least 10, and each of the steam transmitting adjustment layers is formed by stacking a plurality of steam transmitting adjustment paper sheets so that the total thickness of each of the two steam transmitting adjustment layers is 5-25 mm, and a density for each of the steam transmitting adjustment layers is 0.75-0.85 g/cm$^3$, the steam transmitting adjustment paper sheets, which form each of the steam transmitting adjustment layers, are homogenous and have equal thickness, or the steam transmitting adjustment paper sheets in the two steam transmitting adjustment layers, which contact with the sterilization confirmation indicator sheet are a low density steam transmitting adjustment paper sheet having a maximum density of 0.6 g/cm$^3$ and other steam transmitting adjustment paper sheets therein, which are stuck onto the steam transmitting adjustment paper sheets, are a high density steam transmitting adjustment paper sheet having a minimum density of 0.85 g/cm$^3$.

2. The steam sterilization indicator pack according to claim 1, wherein a number of the steam transmitting adjustment paper sheets for forming each steam transmitting adjustment layer is different from each other by 5-10 pieces.

3. The steam sterilization indicator pack according to claim 1, wherein the steam transmitting adjustment paper sheets, which form each of the steam transmitting adjustment layers, are homogeneous and have equal thickness and the thickness thereof is 0.05-0.6 mm.

4. The steam sterilization indicator pack according to claim 1, wherein the pattern is printed on a central region and a circumference region of the sterilization confirmation indicator sheet.

\* \* \* \* \*